Figure 1:
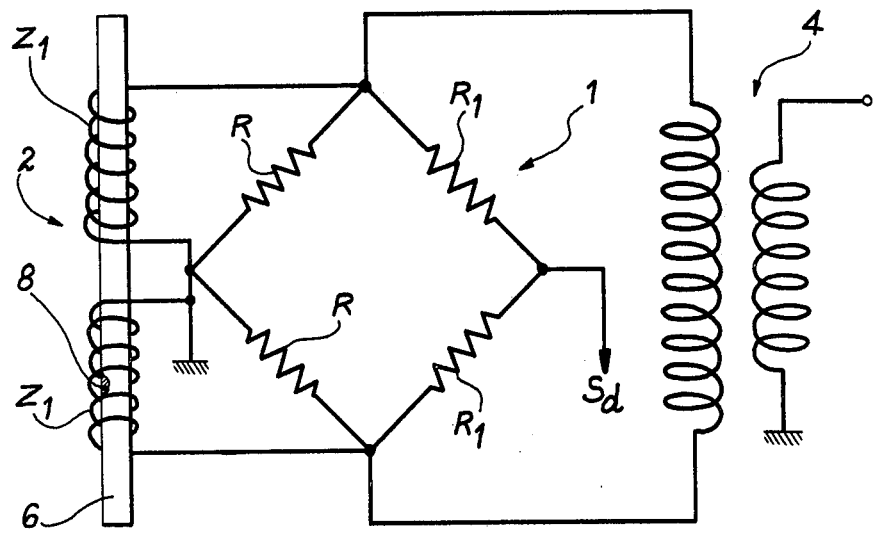

United States Patent [19]

Pigeon et al.

[11] 4,109,201

[45] Aug. 22, 1978

[54] MEASURING BRIDGE FOR AN INSPECTION OR CHECKING DEVICE BY MEANS OF EDDY CURRENTS

[75] Inventors: Michel Pigeon, Bures-sur-Yvette; Robert Saglio, Massy, both of France

[73] Assignee: Commissariat a l'Energie Atomique, Paris, France

[21] Appl. No.: 761,073

[22] Filed: Jan. 21, 1977

[30] Foreign Application Priority Data

Jan. 22, 1976 [FR] France .................... 76 01727

[51] Int. Cl.² .................................. G01R 33/12
[52] U.S. Cl. .......................... 324/227; 324/238
[58] Field of Search ........ 324/34 D, 37, 40, 34 R; 340/196; 323/75 A, 75 C, 75 L

[56] References Cited

U.S. PATENT DOCUMENTS

| 2,794,971 | 6/1957 | Hornfeck | 340/196 |
| 3,599,087 | 8/1971 | Allen et al. | 324/40 |
| 3,961,243 | 6/1976 | Schulz | 324/34 D |
| 4,050,011 | 9/1977 | Mori et al. | 324/40 |

FOREIGN PATENT DOCUMENTS 1,242,747  8/1971  United Kingdom .................... 324/40

OTHER PUBLICATIONS

McMaster, R., Nondestructive Testing Handbook, vol. II, The Ronald Press, N.Y., 1963, p. 37.16.

Primary Examiner—Robert J. Corcoran
Attorney, Agent, or Firm—Cameron, Kerkam, Sutton, Stowell & Stowell

[57] ABSTRACT

Measuring bridge for a device for inspecting or checking by eddy currents of the type comprising a first pair of adjacent branches each constituted by a resistor and a second pair of adjacent branches in parallel with the first pair, whereof at least one of the branches is constituted by a winding which is sensitive to the faults of the part to be inspected, characterized in that it comprises a supplementary resistor connected in parallel on the said winding.

1 Claim, 4 Drawing Figures

MEASURING BRIDGE FOR AN INSPECTION OR CHECKING DEVICE BY MEANS OF EDDY CURRENTS

The present invention relates to a measuring bridge for an inspection or checking device by means of eddy currents.

Measuring bridges for checking or inspection devices by means of eddy currents are known which comprise two resistors and two windings connected in a circuit of the Wheatstone bridge type. If the two windings are sensitive to faults in the member to be checked, the bridge makes it possible to effect a differential measurement. If only one of the windings is sensitive to the faults in the member to be checked, the bridge makes it possible to effect an absolute measurement.

Such bridges make it possible to produce probes which associated with excitation and measuring means can detect faults on members passing in the vicinity of or within windings. In the case where the analysis is performed in an impedance plane each fault leads to the appearance in said plane of a figure of eight shaped curve whose configuration amplitude and inclination make it possible to determine the nature and amplitude of the fault.

The Applicant has found that the addition of a resistor in parallel with the winding or windings sensitive to the faults leads to a surprising action and significant advantages. Thus the addition of such a resistor makes it possible to increase the pass band of the probe, increase the ratio between the signals obtained for a local fault and for a more extensive fault and to render symmetrical the figure of eight shaped response curve.

More specifically the invention has for its object a measuring bridge for a checking or inspection device by means of eddy currents of the type described hereinbefore (absolute bridge or differential bridge) and which is characterised in that it comprises a supplementary resistor connected in parallel to the winding or windings sensitive to the faults in the member to be checked.

According to an advantageous variant, the measuring bridge is duplicated in the sense that it comprises both a differential measuring bridge and an absolute measuring bridge, said two bridges having a common winding which is sensitive in both cases to the faults on the part to be checked, with its supplementary resistor connected in parallel. This double bridge makes it possible to simultaneously carry out a differential measurement and an absolute measurement or if a switch is located between the absolute and differential outputs, either an absolute measurement or a differential measurement.

Figure 2:
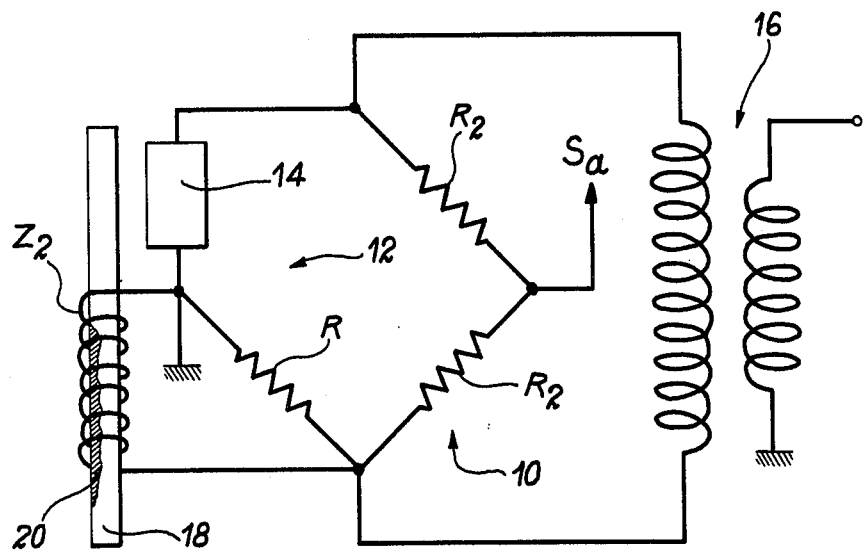
Figure 3:
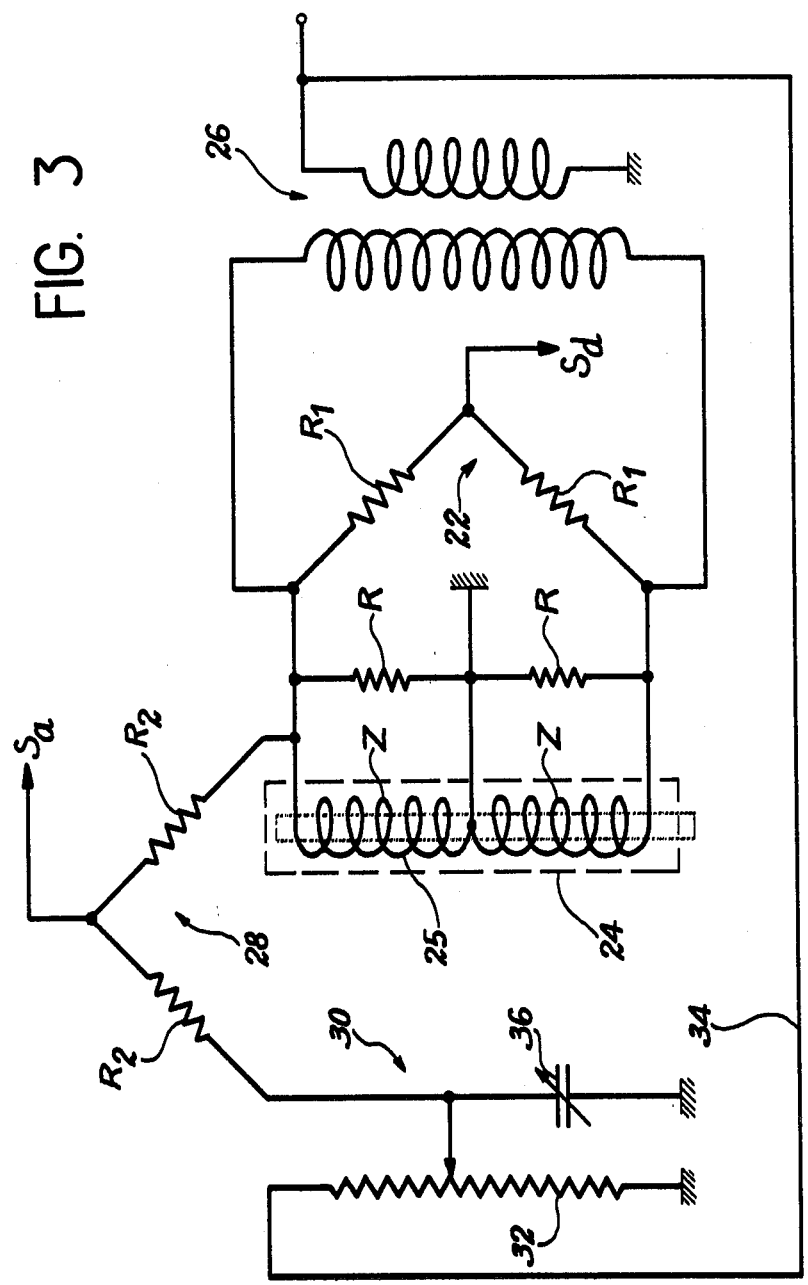
Figure 4:
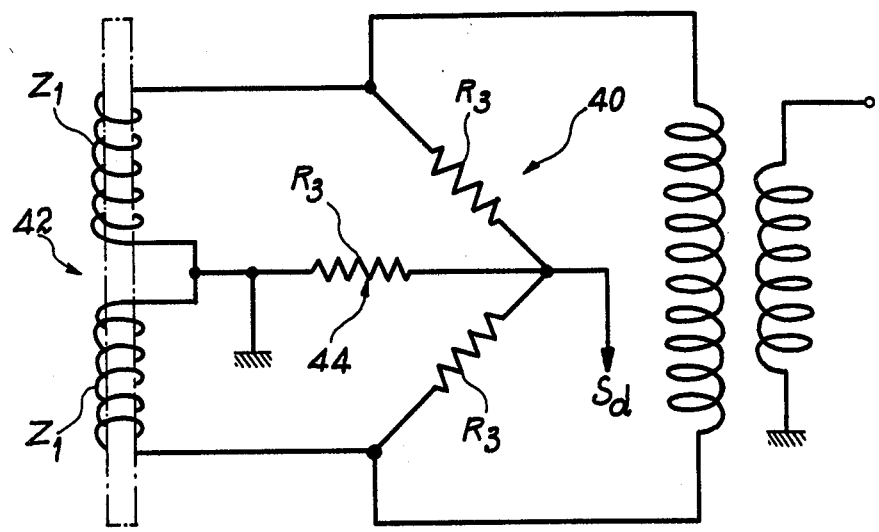

The characteristics and advantages of the present invention can be gathered from the following description with regard to exemplified and non-limitative embodiments with reference to the attached drawings wherein show:

FIG. 1, a differential measuring bridge according to the invention;

FIG. 2, an absolute measuring bridge according to the invention;

FIG. 3, a double absolute and/or differential measuring bridge according to the invention;

FIG. 4, a variant of the bridge according to the invention.

FIG. 1 shows a first variant of the measuring bridge according to the invention making it possible to perform a differential measurement. This bridge comprises a first pair 1 of branches constituted in each case by a resistor of value $R_1$ and by a second pair 2 of branches, each constituted by a winding $Z_1$. According to the invention, each of the windings $Z_1$ is associated with a supplementary resistor R arranged in parallel. The bridge is supplied by means of a transformer 4. The differential measurement is effected by analysing the signal supplied by the output connection $S_d$.

The bridge of FIG. 1 is particularly suitable for checking parts whose faults are of limited size compared with the length of the windings. This is schematically shown in FIG. 1 where the member to be checked carries the reference numeral 6 and where a local fault carries the reference numeral 8. According to the known principle of the differential probe the passage of fault 8 in the two windings successively unbalances the two inductive branches of the bridge and causes variations of the signal appearing on output $S_d$ leading to a figure of eight shaped curve in the impedance plane.

However, the circuit of FIG. 1 is not well suited to the checking of members having more extensive faults and whereby the size of the fault exceeds the length of the two windings. It is obvious that in this case any extensive fault creates two identical unbalances in the two windings so that it is not revealed by a differential bridge. However, this fault can be detected by an absolute measuring bridge like that shown in FIG. 2.

In FIG. 2 the bridge comprises two pairs of branches arranged in parallel whereby the first branch 10 comprises two resistors $R_2$ and the second branch 12 comprises on the one hand a winding $Z_2$ sensitive to the faults of the member to be checked associated with a resistor R in parallel and on the other hand an inductor 14 which is not sensitive to the faults in the member to be checked. Such a bridge is still supplied by a transformer 16 and the absolute measurement is effected by analysing the signal supplied by output $S_a$.

When a member 18 to be checked having a very extensive fault 20 enters winding $Z_2$, branch 12 of the bridge is unbalanced and the fault is revealed.

In order to free the signal measured at the output connection $S_a$ from the exciting voltage of the bridge, it is possible to replace inductor 14 by a circuit permitting the compensation of said exciting voltage as shown in detail in FIG. 3.

FIG. 3 shows a double bridge comprising both an absolute measuring bridge and a differential measuring bridge. The differential measuring bridge comprises a first pair of branches 22 constituted in each case by a resistor $R_1$ and by a second pair of branches 24 constituted in each case by two windings Z. According to the fundamental feature of the invention supplementary resistors are connected in parallel to the two windings Z. The output making it possible to carry out the differential measurement is again designated by $S_d$. The bridge is supplied by a transformer 26.

The part corresponding to the absolute measuring bridge comprises a first pair of branches 28 each constituted by a resistor $R_2$, and by a second pair of branches comprising winding 25 and its associated resistor R and a circuit 30 permitting the compensation of the exciting voltage. This circuit 30 comprises a potentiometer 32 to which, via the connection 34, is applied the supply voltage supplied to transformer 26 and a variable capacitor 36. The regulation of potentiometer 32 and capacitor 36 makes it possible to obtain under no-load conditions the balancing of the absolute bridge in such a way that the voltage appearing on the absolute output connection $S_a$ is free from the exciting signal.

The circuit of FIG. 3 makes it possible to perform either an absolute measurement or a differential measurement using one and the same probe immediately the analytical devices (recorder, oscilloscope etc.) are equipped with a switch connecting them either to output $S_a$ or to output $S_d$.

However, the circuit of FIG. 3 also makes it possible to perform an absolute measurement and at the same time a differential measurement if each of the outputs $S_a$ and $S_d$ is connected to analytical means.

The determination of the value of resistor R arranged in parallel on the windings is not critical but the Applicant has found that it is preferable to select a value for resistor R which is below that of resistors $R_1$ (in the case of a differential bridge) or below that of resistors $R_2$ (in the case of an absolute bridge). For the windings it is also preferable to use inductors whose impedance Z is higher than the value of resistor R.

In an illustrative and non-limitative manner the Applicant has produced a double bridge like that illustrated in FIG. 3 with the following values which have proved satisfactory:

$R_1$ = 1 kOhm
$R_2$ = 10 kOhms
R = 238 Ohms
Z > 238 Ohms

The bridge described hereinbefore can be in various forms provided that they are equivalent from the electrical standpoint. One of these forms is that shown in FIG. 4. In FIG. 4 the bridge comprises a resistive branch 40 formed by two resistors of value $R_3$ and an inductive bridge 42 formed by windings $Z_1$. It also comprises a third resistor 44 of value $R_3$ equal to two others connected between the centre points of the two branches. In this variant each winding $Z_1$ is also associated in parallel with a resistor which is the sum of the value of resistor 44 and of the resistors of branch 40, i.e. two $R_3$.

In place of the numerical values indicated hereinbefore it is possible to use in this variant three resistors of half the value of 238 Ohms for example a standard value of 122 Ohms. If a double bridge is used, the value of $R_2$ remains equal to 10 kOhms.

The advantage of this variant is to decrease the value of resistors $R_1$ of the bridge and to correlatively reduce the value of the impedance offered to the amplifier. The latter then becomes less sensitive to noise and electrical interference.

The bridge of the present invention can be used in any eddy current checking device but is particularly useful in devices according to the earlier dated French Application No. 75 27615 of the present Applicant filed on Sept. 9, 1975 for "Process for non-destructive inspection by eddy currents and corresponding apparatus using multifrequency excitation and permitting the elimination of certain parameters".

As stated hereinbefore, the use of a supplementary resistor R in parallel on the fault-sensitive winding in particular makes it possible to render symmetrical the figure of eight shaped response curve. In this resistor the curve obtained often has an asymmetrical appearance in such a way that the elimination of certain parameters, according to the process described in the above-mentioned French Patent Application, can prove difficult. The use of the resistor according to the present invention considerably facilitates the elimination of undesired parameters.

We claim:

1. Measuring double bridge for a device for inspecting and also checking by eddy currents, said double bridge comprising both an absolute measuring bridge and a differential measuring bridge, said differential measuring bridge comprising a first pair of branches constituted by two resistors R1 and a second pair of branches constituted by two windings, two supplementary resistors R being connected in parallel to the two windings with the midpoints of said resistors R and said windings being grounded, said first pair of branches and said second pair of branches being connected in parallel to a supply transformer, a first output for a differential measuring signal connected between said two resistors R1 of said first pair of branches; said absolute measuring bridge comprising a first pair of branches constituted by two resistors R2 and a second pair of branches constituted by one of said windings of said second pair of branches of said differential measuring bridge connected at its ungrounded end to one end of one of the resistors $R_z$ and by a voltage compensating circuit comprising a variable capacitor grounded at one end and connected at the other end to one end of the other resistor $R_z$ and to the tap of a potentiometer connected to said transformer and a second output for an absolute measuring signal connected between the other ends of said two resistors R2 of said first pair of branches.

* * * * *